United States Patent
Zhou

[11] Patent Number: 6,103,240
[45] Date of Patent: Aug. 15, 2000

[54] HERBAL SWEETENING AND PRESERVATIVE COMPOSITION COMPRISING LICORICE EXTRACT AND MOGROSIDES OBTAINED FROM PLANTS BELONGING TO CUCURBITACEAE AND/OR MOMORDICA

[76] Inventor: James H. Zhou, 32 Hallmark Hill Dr., Wallingford, Conn. 06492

[21] Appl. No.: 09/245,553

[22] Filed: Feb. 5, 1999

[51] Int. Cl.[7] ............................... A01N 65/00; A23L 2/00
[52] U.S. Cl. ......................... 424/195.1; 426/590; 426/599
[58] Field of Search ........................ 424/195.1; 426/590, 426/599

[56] References Cited

U.S. PATENT DOCUMENTS

| | | | |
|---|---|---|---|
| 4,537,763 | 8/1985 | Miyake et al. | 424/49 |
| 4,548,809 | 10/1985 | Fung et al. | 424/52 |
| 5,032,580 | 7/1991 | Watanabe et al. | 514/23 |
| 5,198,427 | 3/1993 | Kinghorn et al. | 514/26 |
| 5,433,965 | 7/1995 | Fisher et al. | 426/548 |
| 5,510,109 | 4/1996 | Tomioka et al. | 424/421 |

OTHER PUBLICATIONS

Chung J.G. Drug and Chemical Toxicology, 1998, 21(3), pp. 355–370.
Grieve M. In: "A Modern Herbal", Edited by Leyel C.F., Barnes and Noble Books, New York, 1996, pp. 487–492.

*Primary Examiner*—Irene Marx
*Assistant Examiner*—Vera Afremova
*Attorney, Agent, or Firm*—Bachman & LaPointe, P.C.

[57] ABSTRACT

An herbal sweetening, preservative and therapeutic composition includes triterpene glycoside composition and extract of licorice, wherein the composition has sweetening and anti-microbial properties, wherein the triterpene glycoside composition is standardized for 80% (wt.) of mogrosides obtained from a plant selected from the group consisting of the members of Cucurbitaceae family, Momordica family and combination thereof, and wherein the extract of licorice is the ethanol soluble and water insoluble fraction. Products including such compositions are also disclosed.

14 Claims, No Drawings

६,१०३,२४०

HERBAL SWEETENING AND PRESERVATIVE COMPOSITION COMPRISING LICORICE EXTRACT AND MOGROSIDES OBTAINED FROM PLANTS BELONGING TO CUCURBITACEAE AND/OR MOMORDICA

BACKGROUND OF THE INVENTION

The invention relates to an herbal composition which has sweetening, preservative and therapeutic properties. There is continued interest in non-sugar natural sweeteners for food, cosmetic and pharmaceutical products, as well as many other products.

Chemical preservatives have been widely used in various products in order to provide such products with longer shelf life. Such chemical preservatives have desirable anti-microbial activity. However, such chemical preservatives are not suitable for use in products which are desired and/or required to contain only natural ingredients.

Thus, the need remains for compositions and products including such compositions which are natural, sugar-free, safe and sweet tasting, and which also have long shelf-life.

It is therefore the primary object of the present invention to provide an herbal composition which provides natural safe sweetening and preservative properties.

It is a further object of the present invention to provide such a composition which is also therapeutic in treating certain conditions.

It is a still further object of the present invention to provide a sweetening and preservative composition, a product including same, and a process for preparing such product, wherein excellent preservative qualities are provided without adversely impacting upon the sweet flavor profile of the composition.

Other objects and advantages of the present invention will appear hereinbelow.

SUMMARY OF THE INVENTION

In accordance with the present invention, the foregoing objects and advantages have been readily attained.

According to the invention, an herbal sweetening and preservative composition is provided, which composition comprises triterpene glycoside and extract of licorice, wherein said composition has sweetening and anti-microbial properties.

A liquid food product is also provided in accordance with the present invention, which product comprises a volume of liquid suitable for human consumption and an herbal sweetening and preservative composition comprising triterpene glycoside, wherein said composition has sweetening and anti-microbial properties.

In further accordance with the present invention, a process is provided for sweetening a liquid product and providing such product with preservative qualities, which process comprises the steps of mixing said liquid product with an herbal composition comprising triterpene glycoside, wherein said composition has sweetening and anti-microbial properties.

DETAILED DESCRIPTION OF PREFERRED EMBODIMENTS

The present invention relates to an herbal sweetening and preservative composition, to food products including such composition and to a process for using such composition to prepare food products having a desired sweetness, as well as a desirably long shelf-life provided by preservative qualities. In addition, compositions according to the invention have certain therapeutic properties.

In accordance with the present invention, it has been found that certain triterpene glycosides naturally possess anti-microbial activity, particularly when combined with small amounts of licorice extract. According to the invention, a composition is provided which comprises an herbal composition including a combination of triterpene glycosides and extract of licorice. End products and processes for sweetening and preserving such end products are also provided.

The triterpene glycosides are preferably glycosides extracted from herbal sources. Preferred triterpene glycosides are extracted from members of the cucurbitacea and/or momordica families, most preferably from momordica grosvenori. The preferred triterpene glycosides are mogrosides which have been found to possess anti-microbial or natural preservative qualities.

Such triterpene glycosides have been found in accordance with the present invention to have an intensely sweet flavor, typically several hundred times sweeter than an equal amount of refined sugar, and also to possess certain anti-microbial properties which can be used to provide products such as food and beverage products with naturally enhanced shelf life.

According to the invention, the most preferred triterpene glycoside is ethanol soluble extract from the aforesaid momordica grosvenori. This extract is also water soluble.

Suitable licorice extract for use in accordance with the present invention may be extract of Chinese licorice or glycyrrhiza uralensis, although other types of licorice may also be used. This licorice extract has been found in accordance with the present invention to have a strong flavor, and an additional anti-microbial activity.

Preferred licorice extract is the ethanol-soluble fraction of licorice extract. This extract is water insoluble.

In accordance with the present invention, it has been found that small amounts of triterpene glycoside and licorice extract in combination are extremely useful in providing a desirable sweet flavor profile, and are also surprisingly effective in combination at providing anti-microbial activity. Specifically, and as will be set forth in the following example, these two components in combination have been found to provide a surprising synergistic anti-microbial activity as compared to the sum of each components' separate anti-microbial activity.

If desired, additional herbal or other types of ingredients can be added to the composition or products prepared in accordance with the present invention. Examples of suitable additional ingredients include diterpene glycosides such as stevioside extracted from Stevia, rubososide extracted from rubus suavisimus, and/or other types of preferably sugar-free sweeteners such as aspartame, saccharin and the like. Depending upon the end use, other carbohydrates, product components, filler materials and the like may also be included.

According to the invention, and in order to provide effective preservative properties, it is preferred that the composition include at least about 0.4 mg/ml of triterpene glycoside and licorice extract combined, more preferably at least about 0.5 mg/ml of triterpene glycoside and licorice extract combined. Most preferably, the composition includes at least about 0.4 mg/ml of triterpene glycoside, and at least about 0.001 mg/ml, preferably at least about 0.01 mg/ml of licorice extract. In some instances, the use of extremely potent licorice as source, or laboratory scale processes can produce an extract which is effective at concentrations as low as 0.001 mg/ml. In commercial scale applications, however, it is more likely that at least about 0.01 mg/ml will be needed.

This concentration of ingredients is based upon concentration in a final liquid product to be naturally preserved according to the invention, and these minimum concentrations have been found to provide excellent anti-microbial activity. For example, such compositions in accordance with the present invention have been found to effectively inhibit growth of microbial matter such as porph gingivails (ATCC 53978), which is representative of an anaerobiotic bacterium, action viscosis (ATCC 19246), and SM 25175, which are representative of aerophilic bacteria. In addition, the herbal composition of the present invention has been found to be an effective agent against $H.$ $pilori$, which is a bacteria causative of stomach ulcer and over production of gastric acid, and $E.$ $coli$ which is a bacteria that causes certain types of diarrhea.

In accordance with the present invention, the intense sweet flavor of triterpene glycoside and the generally unpleasant flavor profile of licorice, when combined according to the invention, provide a desirable intensely sweet profile, while also providing an excellent anti-microbial activity. For example, products including the composition of the present invention as set forth above have been found to possess a shelf-life of at least about 24 months.

The composition of the present invention may suitably be provided in liquid or powder form as a self-preserved sweetener, or may be directly incorporated into food or pharmaceutical products themselves.

In a liquid composition, in order to provide a useful sweet flavor profile, in applications where 100% anti-microbial activity is not necessary, it is preferred to include between about 0.05 mg/ml and about saturated concentration levels of triterpene glycoside in liquid composition, and to include between about 0.001 mg/ml and about 10 mg/ml of licorice extract. Even at minimum values, some anti-microbial activity is also imparted, at least so as to provide a naturally self-preserved sweetener.

In powder form, it is preferred to include at least about 50 ppm of triterpene glycoside, preferably between about 50 ppm and about 100,000 ppm, and at least about 1 ppm, more preferably at least about 50 ppm of licorice extract.

The herbal composition of the present invention may be used as a sweetener having a general chemical composition as set forth in Table 1:

TABLE 1

| | |
|---|---|
| Carbohydrates (including glucose, fructose, maltose and other carbohydrates such as diterpene glycosides) | 1–99.0% (wt.) |
| triterpene glycosides | 0.1–99% (wt.) |
| licorice extract | 0.001–0.5% (wt.) |
| other carbohydrates or fillers | balance |

A preferred herbal composition for use as a sweetener in accordance with the present invention has a composition as set forth in Table 2 below:

TABLE 2

| | |
|---|---|
| Carbohydrates (including glucose, fructose, maltose and other carbohydrates such as diterpene glycoside) | 1–80.0% (wt.) |
| triterpene glycosides | 0.1–20% (wt.) |
| licorice extract | 0.01–0.5% (wt.) |
| other carbohydrates or fillers | balance |

One example of a further preferred sweetener, which would have a strength per weight of approximately 10–30 times that of refined table sugar, is a composition as set forth in Table 3:

TABLE 3

| | |
|---|---|
| fructose | 60–80% (wt.) |
| triterpene glycoside | 0.3–5% (wt.) |
| licorice extract | 0.01–0.5% (wt.) |
| diterpene glycoside | 3–10% (wt.) |
| other carbohydrates, water and other fillers | 1–20% (wt.) |

A sweetener composition according to the invention which has a strength per weight of approximately 20 times that of refined table sugar is as set forth in Table 4:

TABLE 4

| | |
|---|---|
| fructose | 60% (wt.) |
| triterpene glycoside | 3% (wt.) |
| licorice extract | 0.01% (wt.) |
| diterpene glycoside | 6% (wt.) |
| other carbohydrates | 10% (wt.) |
| water and fillers | 20% (wt.) |

A typical liquid product in accordance with the present invention would include a liquid product suitable for human consumption, such as a liquid beverage or pharmaceutical product and the like, with effective amounts of the herbal composition of the present invention mixed or otherwise incorporated therein. For example, such a product could have a composition as follows:

Herbal extracts or other ingredients—2.5–79%(wt.)
triterpene glycosides—0.02–10%(wt.)
Licorice extract—0.01–1% (wt.)
glycerin—0–40%(wt.)
others (flavor, water etc.)—0–60%(wt.)

The composition of the present invention can of course be prepared having a wide range of strength of sweetness. Levels indicated above are those levels preferred for providing the desired anti-microbial activity.

When the composition of the invention is intended for use as a sweetener, for example a powdered sweetener for use as an additive to liquid beverages, it is preferred that the triterpene glycoside and licorice extract be present at a ratio of by weight of triterpene glycoside to licorice extract of between about 3 and about 10, most preferably about 7.

As set forth above, the herbal composition of the present invention has been found to exhibit inhibition against the growth of $H.$ $pilori$, which is currently considered to be a cause of stomach ulcers. In addition, the composition of the present invention has been found to inhibit $E.$ $coli$ growth.

*E. coli* contaminated food is a known cause of symptoms such as diarrhea when such contaminated food is consumed by humans.

The composition of the present invention shows significant improvement in stomach ulcer symptoms such as stomach ache and stomach acid over-production after treatment for approximately 4 weeks. Improvement was experienced using a 40 mg dose three (3) times per day, and even better results were obtained using a 120 mg dose three (3) times per day.

The composition of the present invention at similar dosages also stopped diarrhea caused by *E. coli*—contaminated food after treatment for 1–3 days.

The composition of the present invention when used as treatment for stomach ulcer symptoms and *E. coli*—contamination symptoms may typically be administered as a liquid, powder and the like containing between about 30% (wt.) and about 70%(wt.) of triterpene glycoside, and between about 25%(wt.) and about 50%(wt.) of licorice extract, with the balance being fillers, flavoring, carriers and the like.

The following example illustrates the excellent inhibition results obtained against microorganisms through use of the composition of the present invention.

EXAMPLE

In this example, a composition in accordance with the present invention including a 0.5%(w/v) concentration of triterpene glycoside composition (80%wt triterpene glycoside, referred to in Table 7 as "HS10") and a 0.5% (w/v) of licorice extract (referred to in Table 7 as "Lr3") were tested for inhibition of the bacterias PG53978 and SM36668. Each of these ingredients were also tested for inhibition of such microorganisms separately.

The triterpene glycoside used was water and ethanol soluble mogroside extracted from momordica grosvenori, and the licorice extract was the ethanol soluble fraction of extract of glycyrrhiza uralensis. Table 5 below indicates the minimum inhibition concentrations (MIC), in terms of milligrams of composition per milliliter of total test volume (mg/ml), which were required to obtain 100% neutralization of the aforesaid bacteria in said test volume.

The MIC in terms of gg/ml is determined by the following relationship:

MIC($\mu$g/ml)=(CONC.%)·(1g/100ml)·(1E6$\mu$g/1g)·(1/dissolution).

The MIC is determined by starting with a known effective quantity of material, and gradually increasing the dissolution factor until a concentration is reached where 100% inhibition is not obtained. The immediately preceding MIC value is the minimum inhibition concentration of the agent in question.

This value can alternatively be presented in milligrams per milliliter, as set forth below in Table 5.

TABLE 5

| Inhibitor Name | Alone MIC | Combination MIC | Actual Product Examples | | |
|---|---|---|---|---|---|
| | | | Blackberry extract | Soy extract | green tea extract |
| Glycyrrhia Uralensis | 0.7 mg/ml | 0.1 mg/ml | 1 mg/ml | 1 mg/ml | 1 mg/ml |
| triterpene glycoside comp. (actual triterpene glycoside) | 1.3 mg/ml (1.04 mg/ml) | 0.7 mg/ml (0.56 mg/ml) | >5–8mg/ml | >3–5 mg/ml | 14 mg/ml |

As shown, licorice extract alone had an MIC of 0.7 mg/ml. and the triterpene glycoside composition alone had an MIC of 1.3 mg/ml. However, a combination of these two ingredients surprisingly provided inhibition with 0.1 mg/ml licorice extract and 0.7 mg/ml triterpene glycoside composition. Thus, a far smaller total concentration of composition in accordance with the present invention can be used as compared to each ingredient alone.

The right hand portion of Table 5 shows the typical range of ingredients of triterpene glycoside and licorice extract for three typical products, specifically blackberry extract, soy extract and green tea extract, which could be provided in accordance with the present invention having desired sweetness flavor profile and also excellent inhibition of microorganisms.

From MIC values, a fractional inhibitory concentration (FIC) can be determined, which is a useful indicator of the effectiveness of a particular combination of components as compared to the components individually.

FIC is determined as follows:

$$FIC = \frac{MIC\ A(\text{combination})}{MIC\ A(\text{alone})} + \frac{MIC\ B(\text{combination})}{MIC\ B(\text{alone})}$$

The effectiveness of a combination can be determined from its FIC, and the lower the value of the FIC, the more effective is the combination. Table 6 below sets forth a general convention indicating the level of synergy corresponding to a particular FIC.

TABLE 6

| | |
|---|---|
| Highly Synergistic Combination: | FIC <= 0.5 |
| Synergistic Combination: | FIC 0.5–0.75 |
| Partially Synergistic Combination: | FIC 0.75–1.0 |
| Additive Combination: | FIC > 1.0–2.0 |

The composition of the present invention in combination, as well as each ingredient alone, as used for the data set forth in Table 5 above, were tested for inhibition of bacteria. Two representative strains of bacteria, specifically PG53978 and SM35668, were used. The particular bacteria was grown in a liquid microbial broth, and the particular composition to be tested was dissolved in methanol and incubated with the bacteria for a period of 48 hours. Following incubation, samples were assayed in a 96well plate. The well plate was read under a vision light reader at 550 nm wavelength, and the density of each well represented the growth of indicated bacteria. Table 7 below sets forth the minimum concentration of each composition alone, and in combination, which was required to inhibit such bacteria growth by 100%. Table 7 also presents the FIC for the combination, which clearly shows a synergistic combination.

TABLE 7

| Test strains | Alone MIC | | Combination MIC | | | Reduction |
| --- | --- | --- | --- | --- | --- | --- |
| | 0.5% HS10 | 0.5% Lr3 | 0.5% HS10 | 0.5% Lr3 | FIC | from alone |
| PG 53978 | 1250.0 | 78.1 | 625.0 | 19.5 | 0.750 | 48.5% |
| SM 35668 | 625.0 | 312.5 | 312.5 | 78.1 | 0.750 | 41.7% |
| MEAN | 937.5 | 195.3 | 468.8 | 48.8 | 0.749 | 45.7% |

As shown, drastically smaller levels of each ingredient were required when used together in order to obtain 100% inhibition of bacteria growth. This advantageously allows for the use of less potentially expensive ingredients, as well as a smaller concentration per unit product of licorice extract, which above certain levels would provide an undesirable flavor. In addition, the anti-microbial resistance provided by such low levels of triterpene glycoside and licorice extract allow for other non-antimicrobial components to be included in the composition or product of the present invention, for example to provide additional flavor and the like.

As shown in Table 7, the composition of the present invention illustrated a mean FIC of 0.749, which clearly is indicative of a synergistic combination. Certainly, the combination of ingredients in accordance with the present invention is surprisingly effective at surprisingly low levels in connection with inhibition of microorganisms.

This invention may be embodied in other forms or carried out in other ways without departing from the spirit or essential characteristics thereof. The present embodiment is therefore to be considered as in all respects illustrative and not restrictive, the scope of the invention being indicated by the appended claims, and all changes which come within the meaning and range of equivalency are intended to be embraced therein.

What is claimed:

1. An herbal sweetening and preservative composition having sweetening and anti-microbial properties and comprising about 0.1–99% (wt.) of a triterpene glycoside composition and at least about 0.001% (wt.) of an extract of licorice, wherein the triterpene glycoside composition is standardized for 80% (wt.) of mogrosides obtained from a plant selected from the group consisting of the members of Cucurbitaceae family, Momordica family and combination thereof, and wherein the extract of licorice is the ethanol soluble and water insoluble fraction.

2. The herbal sweetening and preservative composition according to claim 1 wherein said mogrosides are obtained from *Momordica grosvenori*.

3. The herbal sweetening and preservative composition according to claim 1 wherein the extract of licorice is obtained from *Glycyrrhiza uralensis*.

4. A liquid food product comprising a volume of a liquid suitable for human consumption and an effective amount of a herbal sweetening and preservative composition comprising a least about 0.4 mg of a triterpene glycoside composition per milliliter of the liquid food product and at least about 0.001 mg of an extract of licorice per milliliter of the liquid food product, wherein the triterpene glycoside composition is standardized for 80% (wt.) of mogrosides obtained from a plant selected from the group consisting of the members of Cucurbitaceae family, Momordica family and combination thereof, wherein the extract of licorice is the ethanol soluble and water insoluble fraction, and wherein the herbal sweetening and preservative composition has sweetening and anti-microbial properties.

5. The product of claim 4, wherein said triterpene glycoside composition and said extract of licorice are present at a concentration of at least about 0.5 mg per milliliter of product.

6. The product of claim 4, wherein said triterpene glycoside composition is present at a concentration of at least about 0.5 mg per milliliter of product, and wherein said extract of licorice is present at a concentration of at least about 0.01 mg per milliliter of product.

7. The product of claim 4, wherein said extract of licorice is extract of *Glycyrrhiza uralensis*.

8. The product according to claim 4, wherein said herbal sweetening and preservative composition is effective in inhibiting growth of microorganisms.

9. The product of claim 4, wherein said mogrosides are obtained from *Momordica grosvenori*.

10. A process for sweetening and preserving a liquid product comprising the step of mixing said liquid product with a herbal sweetening and preservative composition comprising a least about 0.4 mg of a triterpene glycoside composition per milliliter of the liquid food product and at least about 0.001 mg of an extract of licorice per milliliter of the liquid food product, wherein the triterpene glycoside composition is standardized for 80% (wt.) of mogrosides obtained from a plant selected from the group consisting of the members of Cucurbitaceae family, Momordica family and combination thereof, wherein the extract of licorice is the ethanol soluble and water insoluble fraction, and wherein the herbal sweetening and preservative composition has sweetening and anti-microbial properties.

11. The process of claim 10, wherein said triterpene glycoside composition and said extract of licorice are present at a concentration of at least about 0.5 mg per milliliter of product.

12. The process of claim 10, wherein said triterpene glycoside composition is present at a concentration of at least about 0.5 mg per milliliter of product, and wherein said extract of licorice is present at a concentration of at least about 0.01 mg per milliliter of product.

13. The process according to claim 10, wherein said herbal sweetening and preservative composition is effective in inhibiting growth of microorganisms.

14. The process of claim 10, wherein said mogrosides are obtained from *Momordica grosvenori*.

* * * * *